United States Patent [19]

Holtkamp, Sr.

[11] Patent Number: Plant 7,331

[45] Date of Patent: Sep. 18, 1990

[54] AFRICAN VIOLET PLANT NAMED EVERGLADES

[76] Inventor: Reinhold Holtkamp, Sr., Blumenstrasse 28, D 4242 Rees-Haffen, Fed. Rep. of Germany

[21] Appl. No.: 363,465

[22] Filed: Jun. 8, 1989

[51] Int. Cl.[5] ..... A01H 5/00

[52] U.S. Cl. ..... Plt./69

[58] Field of Search ..... Plt./69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of African violet named Everglades characterized by its single violet-shaped to semi-double, blue flowers with frilled edges; strong, upright flower stems that curve slightly toward the center to form a compact bouquet above the leaves; large medium green leaves, profuse flowering, vigorous growth habit, flowering 10–11 weeks after potting, and its long lasting and non-dropping flowers.

1 Drawing Sheet

The present invention comprises a new and distinct cultivar of African violet plant, botanically known as *Saintpaulia ionantha,* and hereinafter referred to by the cultivar name Everglades.

The new cultivar was referred to during the breeding and selection process by the designation H 81/10 and is a product of a planned breeding program. The new cultivar was orginated from a cross made by me in the controlled breeding program in Haffen, Federal Republic of Germany. The female, or seed parent was a cultivar designated C 81/1. The male, or pollen parent was a cultivar designated 219/3.

Everglades was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Everglades has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Everglades, which in combination distinguish this African violet as a new and distinct cultivar:

(1) Strong, upright flower stems curving slightly toward the center.

(2) Single to semi-double blue flowers with frilled edges.

(3) Profuse flowering.

(4) Each plant carries 7–9 and more upright flower stems each of which carries 8–10 and more flowers.

(5) Long lasting, non-dropping flowers.

(6) Vigorous grower.

(7) Plant saleable 10 to 11 weeks after potting.

(8) Seed capsules push slightly through.

(9) Large, medium green leaves.

(10) After maturity the flowers dry off, and remain on the peduncle without becoming infected by botrytis.

Everglades is similar in certain respects to Shenandoah, disclosed in U.S. Plant Pat. No. 6,526. The color and shape of the blooms and the leaves of Shenandoah and Everglades are similar. However, whereas Shenandoah always has semi-double, wavy blooms, Everglades has mostly single, occasionally semi-double blooms, and frilled edges. Everglades is also distinguished by its somewhat lighter flower color, and lack of serration on the leaves.

The accompanying color photographic drawing shows a typical specimen plant of the new cultivar. The colors appearing in the photograph are as true as possible with color illustrations of this type.

In the following description, color references are made to The Royal Horicultural Society Colour Chart (R.H.S.), except where general colors of ordinary significance are referred to. Color values were taken under natural sunlight conditions at approximately 12 p.m. in Nashville, Tenn.

Botanical Classification: *Saintpaulia ionantha,* Ramat., c.v. Everglades.

Parentage:

*Male parent.*—219/3.

*Female parent.*—C 81/1.

Propagation: The new cultivar holds its distinguishing characteristics through successive propagations by leaf cuttings.

Plant: From 8 to 10 cm tall when grown in pots, and approximately 24–27 cm in diameter when fully grown.

*Leaves.*—General form: Oval to heart-shaped. Diameter: 65–80 mm wide and 75–90 mm long. Texture: Velvety. Aspect: Hairy, slightly shiny. Veins: Upperside: visible; underside: well pronounced, light green, shiny. Color (upperside): Yellow-Green Group 147 A. Color (underside): Greyed-Green Group 194 D. Petiole: Strong upright, brownish green, hairy.

*Flowers.*—Buds: Bell-shaped, 7–8 mm just before opening. Sepals; Five (5). Color: Brownish green. Calyx: Shape: Funnel-shaped. Aspect: Spear-shaped, hairy. Peduncle: Character: Strong upright, hairy. Color: Brownish green.

Individual flowers: Size: 35–40 mm. Shape: Single violet-shaped to semi-double (having 2–5 additional petals of various sizes), frilled edges. Color (upperside): Violet-Blue Group 93 B to C. Under cooler temperatures and more intensive lighting, the blue color tends to intensify. Color (underside): Violet Group 88 C to D. Borne: Each flower stem carries 8–10 and more flowers on strong, upright peduncle that are free standing above the leaves, thereby forming a compact bouquet. Flowering habit: Flowers 10–11 weeks after potting.

*Reproductive organs.*—Stamens: Two (2). Anthers: 2 composed of 4 anther cells, seed capsule pushes slightly through. Filaments: Yellowish green with blue on edges, 3 mm. long. Pollen Color: Yellow Group 7 A. Styles: 5–6 mm long, purplish blue, base of ovary light green and hairy.

*Roots.*—Normally developed, white when young, turning slightly brownish when older.

Disease resistance: Good.

General observations: Everglades is an attractive, vigorous grower with large, medium green leaves. A tight bouquet of blue flowers free standing above the leaves develops after approximately 10–11 weeks. Each of the 7–9 and more strong flower stems carries 8–10 and more single violet-shaped to semi-double flowers (having 2–5 additional flowers of various sizes) with frilled edges. The anthers are occasionally covered up. The flowers are long-lasting and non-dropping and the seed capsules push slightly through.

I claim:

1. A new and distinct cultivar of African violet named Everglades, as described and illustrated, and particularly characterized by its single violet-shaped to semi-double, blue flowers with frilled edges; strong, upright flower stems that curve slightly toward the center to form a compact bouquet above the leaves; large medium green leaves, profuse flowering, vigorous growth habit, flowering 10–11 weeks after potting, and its long lasting and non-dropping flowers.

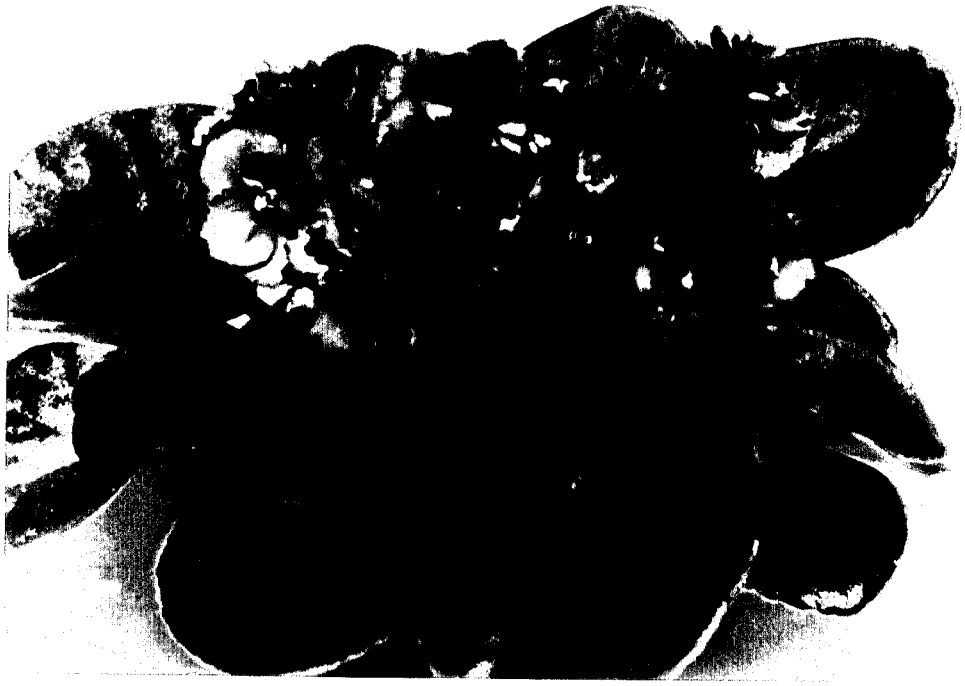

* * * * *